US008332012B2

(12) United States Patent
Kienzle, III (10) Patent No.: US 8,332,012 B2
(45) Date of Patent: *Dec. 11, 2012

(54) APPARATUS AND METHOD FOR IMPROVING THE ACCURACY OF NAVIGATED SURGICAL INSTRUMENT

(75) Inventor: Thomas C. Kienzle, III, Lake Forest, IL (US)

(73) Assignee: General Electric Company, Schenectady, NY (US)

( * ) Notice: Subject to any disclaimer, the term of this patent is extended or adjusted under 35 U.S.C. 154(b) by 1815 days.

This patent is subject to a terminal disclaimer.

(21) Appl. No.: 11/100,298

(22) Filed: Apr. 6, 2005

(65) Prior Publication Data
US 2005/0288679 A1 Dec. 29, 2005

Related U.S. Application Data

(63) Continuation of application No. 10/756,020, filed on Jan. 12, 2004, now Pat. No. 6,922,581, which is a continuation of application No. 09/683,107, filed on Nov. 19, 2001, now Pat. No. 6,718,194.

(60) Provisional application No. 60/249,697, filed on Nov. 17, 2004.

(51) Int. Cl.
*A61B 5/05* (2006.01)

(52) U.S. Cl. ......................... 600/424; 600/427; 600/429

(58) Field of Classification Search .................. 600/426, 600/427, 424, 429
See application file for complete search history.

(56) References Cited

U.S. PATENT DOCUMENTS

| 5,769,092 A | 6/1998 | Williamson, Jr. |
| 5,799,055 A * | 8/1998 | Peshkin et al. ................... 378/42 |
| 6,167,296 A | 12/2000 | Shahidi |
| 6,226,548 B1 * | 5/2001 | Foley et al. ................... 600/426 |
| 6,301,495 B1 | 10/2001 | Gueziec et al. |
| 6,370,418 B1 * | 4/2002 | Bernoski ....................... 600/426 |
| 6,415,171 B1 | 7/2002 | Gueziec et al. |
| 6,447,448 B1 | 9/2002 | Ishikawa |

(Continued)

FOREIGN PATENT DOCUMENTS

WO 0047103 A2 8/2000

(Continued)

OTHER PUBLICATIONS

EP International Search Report Application No. 02725686.6 Aug. 7, 2009 (4 pages).

*Primary Examiner* — Long V. Le
*Assistant Examiner* — Ellsworth Weatherby
(74) *Attorney, Agent, or Firm* — McAndrews, Held & Malloy, Ltd.; William Baxter (57) ABSTRACT

A computer assisted surgery system is described for assisting a surgeon in aligning a drill with the interlocking holes of an implanted intramedullary (IM) rod used for fixation of long bone fractures. With the IM rod inserted, a localizing device measures the pose of a tracked adapter attached to the rod's exposed end. Approximate AP and lateral fluoroscopic x-ray images are acquired of the end of the rod with the interlocking holes. Image processing algorithms determine the actual position of the rod and calculate an adjustment to the pose of the tracked adapter and IM rod. Using the adjusted pose information, the system displays, in three roughly orthogonal views, a representation of the drill trajectory relative to the images of the IM rod and relative to a graphic representation of the IM rod.

29 Claims, 5 Drawing Sheets

U.S. PATENT DOCUMENTS

| | | |
|---|---|---|
| 6,470,207 B1 * | 10/2002 | Simon et al. .................. 600/426 |
| 6,505,062 B1 | 1/2003 | Ritter et al. |
| 6,654,629 B2 | 11/2003 | Montegrande |
| 6,697,664 B2 | 2/2004 | Kienzle, III et al. |
| 6,773,437 B2 | 8/2004 | Ogilvie et al. |
| 6,922,581 B2 | 7/2005 | Kienzle, III |
| RE39,133 E | 6/2006 | Clayton et al. |
| 7,117,027 B2 | 10/2006 | Zheng et al. |
| 2005/0288679 A1 | 12/2005 | Kienzle, III |

FOREIGN PATENT DOCUMENTS

| | | |
|---|---|---|
| WO | 0047103 A3 | 8/2000 |
| WO | 03043485 A2 | 5/2003 |
| WO | 03043485 A3 | 5/2003 |

* cited by examiner

APPARATUS AND METHOD FOR IMPROVING THE ACCURACY OF NAVIGATED SURGICAL INSTRUMENT

RELATED APPLICATIONS

This application is a continuation of U.S. application Ser. No. 10/756,020, filed Jan. 12, 2004, titled "Computer Assisted Intramedullary Rod Surgery System with Enhanced Features," issued on Jul. 26, 2005 as U.S. Pat. No. 6,922,581, which is a continuation of U.S. application Ser. No. 09/683,107, filed Nov. 19, 2001, issued on Apr. 6, 2004 as U.S. Pat. No. 6,718,194, titled "Computer Assisted Intramedullary Rod Surgery System With Enhanced Features," which claims the benefit of U.S. Provisional Application No. 60/249,697 filed Nov. 17, 2000, all of which are hereby incorporated in their entireties.

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

This invention relates to a computer assisted surgery system for use in inserting interlocking screws in an intramedullary rod.

A current surgical treatment for fractures of the shaft of long bones (e.g., femur and tibia) is the insertion of an intramedullary rod (IM rod). These devices are relatively rigid devices inserted into one end of the bone and down the center canal of the bone shaft, such that the fracture site is bridged. Transverse holes in either end of the IM rod receive screws inserted transversely through the bone in order to lock the two bone fragments relative to one another. The insertion of the screws farthest from the IM rod insertion hole is currently a difficult and time consuming procedure requiring numerous x-ray images. An intraoperative x-ray machine (C-arm) is repeatedly fired and reoriented until it is exactly aligned with the transverse holes as evidenced by x-ray images displaying the holes as "perfect circles". To establish a starting point, the surgeon uses further x-ray images to align the drill tip with the images of the holes. The surgeon then uses the source-to-receiver axis of the C-arm as an external reference frame along which the long axis of the drill is oriented. Even after this, several attempts may be required to drill the holes into the bone and through the transverse holes.

Several alternative approaches have been employed in an attempt to speed this process. External jigs have been tried with little success because inaccuracies in the jig, inaccuracy of the mounting between jig and IM rod, and deformation of the IM rod accumulate to cause the final jig hole positions to be unreliably aligned with the IM rod holes. Radiolucent drills and drill guides and laser sighting devices have been developed which, in the best cases, improve the speed and accuracy of hole placement, but still require a significant number of x-ray images to be obtained in order to first achieve a C-arm orientation that produces "perfect circles" in the images.

Image-guided approaches have been developed, but these too require the "perfect circle" alignment of the C-arm. Most image guided systems display the drill trajectory over "perfect circle" images of the IM rod. One system assists the surgeon in correctly orienting the C-arm to obtain "perfect circles": "Surgical Navigation Based on Fluoroscopy Clinical Application for Computer-Assisted Distal Locking of Intramedullary Implants", Suhm, et.al., Computer Aided Surgery 5:391-400, 2000. Another difficulty with existing image guided systems is that the surgeon must align the drill guide while viewing an "end on" representation of the drill guide, which can be quite challenging.

Several devices have been described (U.S. Pat. Nos. 5,411,503, 5,540,691, 6,074,394, 6,081,741) in which an emitter is inserted into the IM rod, down to the level of the interlocking holes, and transducers on the drill guide report the position of the drill trajectory relative to the holes. These devices, however, require equipment dedicated to this one surgical task, require the extra step of inserting an emitter to the level of the hole, and typically provide only rudimentary "end on" representations of the drill trajectory.

U.S. Pat. No. 6,285,902, incorporated herein by reference, entitled "Computer Assisted Targeting Device for Use in Orthopaedic Surgery" describes a system in which, preferably, orthopedic surgical tools outfitted with infrared LEDs are tracked by an optical localizing device. The poses of these tools are determined and graphic representations of the tools are superimposed on standard intraoperative x-ray images. This allows the surgeon to view, in real time, the position of the tool or tools with respect to an imaged body part or another tool or tools. In the preferred embodiment, a drill guide outfitted with infrared LEDs is tracked and the trajectory of its bore is displayed on the x-ray image of the involved bone. This allows a surgeon to accurately predict the trajectory of a guide pin that passes through the bore of the drill guide. The guide pin, once inserted, is used as a reference for the insertion of implantable cannulated screws.

An alternative embodiment of the previous invention, described in the referenced patent, allows its use in the insertion of distal interlocking screws in an intramedullary (IM) rod by displaying the drill guide trajectory relative to a computer generated representation of a cross-section of the IM rod. The current invention is an enhancement to the previous invention that adjusts the graphic representations of the IM rod based on information developed from the x-ray images. This facilitates the more accurate alignment of a drill through the holes and eliminates the need to align the x-ray beam with the holes in the IM rod. This can significantly reduce the amount of radiation involved in the procedure and reduce the time required to insert the screws.

BRIEF SUMMARY OF THE INVENTION

Accordingly, one objective of the present invention is to provide a computer assisted surgery system for positioning an instrument relative to a portion of a surgical implant. More specifically, it assists a surgeon in drilling a hole through a long bone and through transversely oriented holes in an intramedullary rod (IM rod) during a fracture fixation procedure regardless of deformation of the IM rod.

Another objective of the invention is to provide a technique and apparatus for accurately displaying the trajectory of the drill relative to the holes of the IM rod.

Still another objective of the invention is to provide a technique and apparatus for using x-ray images of the IM rod to accurately determine the locations of the holes.

These and other objects of the present invention are achieved by the use of a computer assisted surgery system, including a computer, a localizing device and a display monitor. The system also includes a tracked adapter attached to the IM rod and a drill guide, both of which have their poses determined by the localizer. With the IM rod inserted in a long bone, and the tracked adapter attached to the exposed end of the IM rod the pose of the adapter and the IM rod are measured by the localizing device. Two approximately orthogonal x-ray images are then obtained of the IM rod in the vicinity of the holes. Image processing techniques are used to accurately determine the location of the IM rod from the x-ray images and an adjusted pose is calculated for the IM rod. A graphic representation of the drill trajectory is displayed superimposed over the images of the IM rod and over a graphic representation of the IM rod, in order to assist the surgeon in placing the drill in the proper position relative to the IM rod holes.

DETAILED DESCRIPTION OF THE INVENTION

Figure 1:
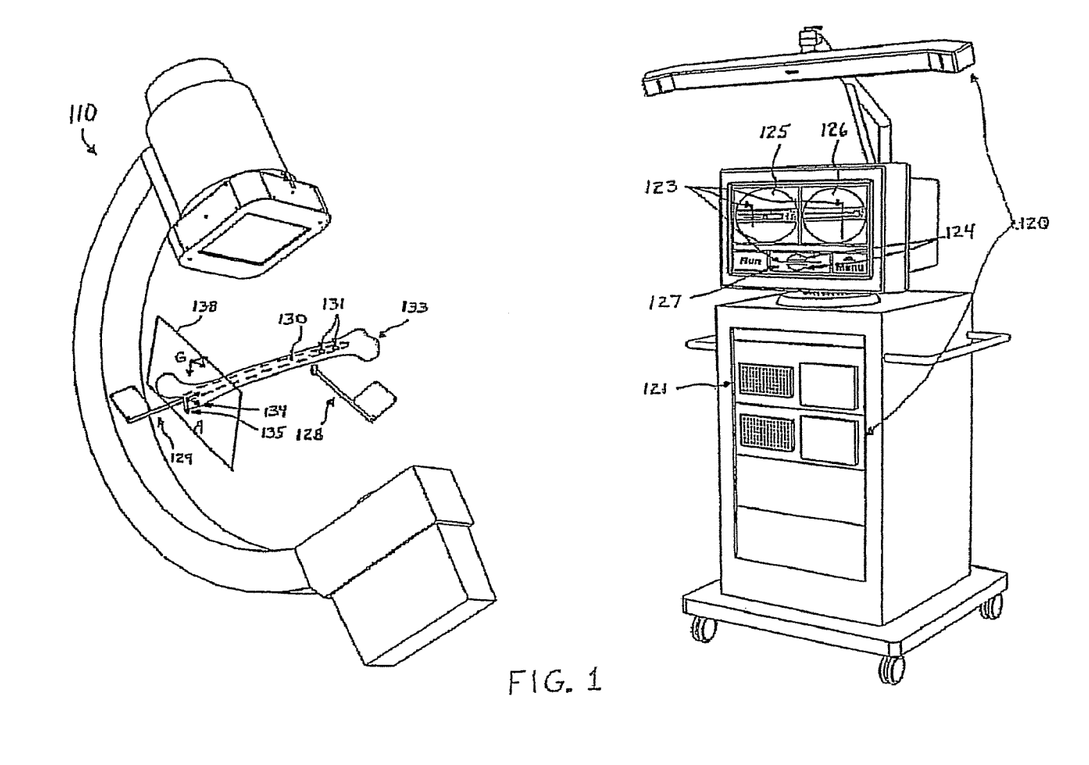
FIG. 1 is a perspective view of an intramedullary rod inserted into a femur, a tracked adapter attached to the intramedullary rod, a drill guide, a partial C-arm, the computer assisted surgery system with localizer camera and display screen containing images and graphics.

An embodiment of the image guided system of U.S. Pat. No. 6,285,902 teaches a system for placing distal interlocking screws in an IM rod. As shown in FIG. 1, the system is based on a computer (121) that receives input from an x-ray imaging device (110) and a localizing device (120), and displays surgical instrument representations (123) over x-ray images (125 and 126) in real time. A tracked adapter (129) is attached to the exposed end of the inserted IM rod (130) such that the pose of the rod can be tracked. A drill guide (128) is also tracked, and a representation of its trajectory (123) is overlaid on x-ray images (125 and 126) of the IM rod (130). Additionally, the system displays, in a separate window (127), the drill guide trajectory (123) relative to a graphical representation (124) of a cross-section of the IM rod (130) at the level of the transverse interlocking holes (131) by projecting models of these instruments onto a picture plane (138). During the procedure, the surgeon uses the AP image (126) of the IM rod (130) to align the drill guide (128) in the coronal plane, and the lateral image (125) and the cross sectional graphic (124) to align the drill guide (128) in the axial plane.

Figure 2:
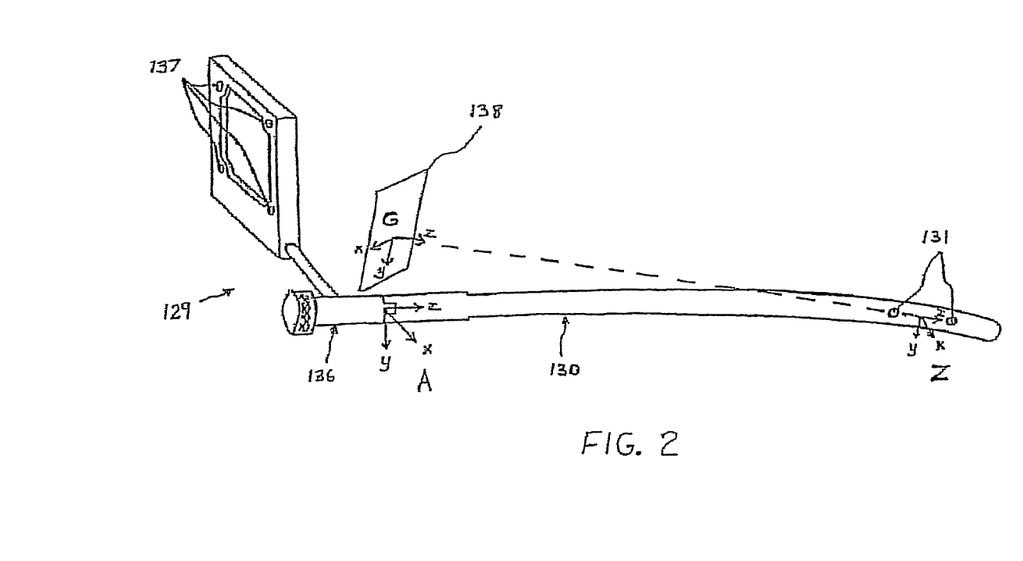
FIG. 2 is a perspective view of the intramedullary rod with attached tracked adapter.

The current invention improves upon the previous invention by providing greater accuracy in generating the graphic representations (124) of the IM rod (130) relative to the drill guide (128), regardless of bending of the IM rod (130) or minor errors in attaching the adapter (129) to the IM rod (130). This improvement allows the surgeon to use these relative graphic representations (124 and 123) alone to exactly align the drill guide (128) in the axial plane. While the surgeon still uses the AP view (126) to align the drill guide (128) in the coronal plane, there is no longer a need to rely on the lateral view (125), thus avoiding the difficulty of positioning a drill guide (128) using an "end-on" representation, during the axial alignment of the trajectory. It also eliminates the need for the surgeon to estimate the required anteroposterior position of the drill guide tip based on the distance between the IM rod and the femoral shaft cortex and the amount of axial rotation of the IM rod. In the preferred embodiment, the IM rod (130) is inserted in the long bone (133) in the usual manner. While the invention will be preferably described for drilling holes in the bone (133) for the interlocking holes (131) in the end of the IM rod farthest from the exposed end, the system may be alternately used for all interlocking screws and associated implants. As shown in FIG. 2, a tracking device (129), preferably comprising an adapter (136) to the IM rod (130) and an array of three or more localizing emitters (137), is attached to the exposed end of the IM rod (130). The exposed end of the IM rod (130) is keyed to the adapter (136) such that the adapter (136) is attached to the inserted rod in a unique manner and the relationship is known within the limits of error of attachment preferably to within a few degrees and a few millimeters. A coordinate frame, A, is defined preferably at the interface between the IM rod (130) and the tracking device (129) and is in a known and fixed relationship to the localizing emitters (137). Computer models of the features of the tracking adapter (129) and IM rod relative to coordinate frame A and graphic representations of features of the IM rod (130) relative to coordinate frame A are stored in the computer's long term memory. A second coordinate frame, Z, is defined relative to the localizing emitters (137) of the tracking device (129) and is preferably located on the IM rod (130) halfway between the transverse holes (131). It is oriented with the z-axis coincident to the long axis of the IM rod (130) and the x-axis parallel to the bore of the transverse holes (131). Another coordinate frame, G, is selected relative the localizing emitters (137) such that its x-axis and y-axis define a picture plane (138) upon which instrument representations may be projected to form an image for display. The z-axis of coordinate frame G is preferably oriented such that it passes through the centers of both distal transverse holes (131), thus causing representations of both distal transverse holes (131) to project to the same location on the picture plane (138). Alternatively, the picture plane (138) may be selected in any pose that is near-orthogonal (e.g., within 20 degrees) to the long axis of the IM rod without departing from the instant invention. Further, separate picture planes may be selected for each transverse hole through which the system is to assist the surgeon in inserting a screw.

Figure 3:
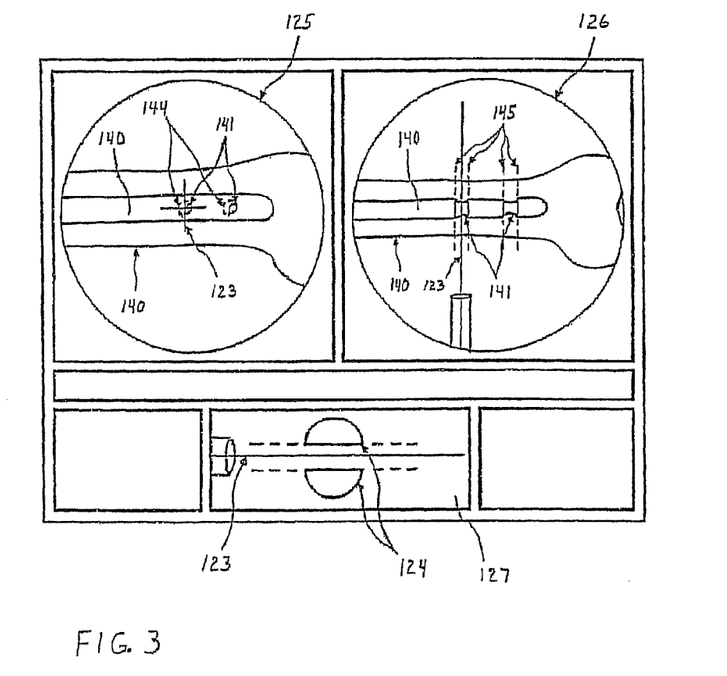
FIG. 3 is an example of a screen display of two images and a generated graphic with superimposed instrument representations.

With the tracking device (129) attached to the IM rod (130) and its pose being read by the localizing device, a graphic representation of the IM rod (130) is projected onto the picture plane (138) defined by coordinate frame G. Because the picture plane (138) is defined to be substantially perpendicular to the long axis of the IM rod (130), the image projected on it will be an "end-view" of the IM rod graphic representation. This end-view image is projected onto the picture plane (138) and, as shown in FIG. 3, is transformed into a graphic representation (124) of the IM rod and displayed in a field (127) of the display screen. The software can display different versions of an instrument representation for different viewing angles. The end-view version of the IM rod representation (124) is a pair of semicircles representing the cross section of the IM rod (130) with a gap between them representing the transverse holes (131). Virtual lines are additionally displayed as dashed lines extending from the straight portion of the semicircles to emphasize the orientation of the transverse screw holes (131). The purpose of this representation (124) is to provide the surgeon with improved information regarding the orientation and location of the transverse holes (131) in the axial plane.

Returning to FIG. 1, the C-arm (110) acquires x-ray images (125 and 126) of the bone (133) that include the transverse holes (131) of the inserted IM rod (130). These images (125 and 126) need not be exactly anteroposterior or exactly lateral with respect to the IM rod (130) (i.e., "perfect circles" need not be obtained). The C-arm (110) need be oriented only to within about 30 degrees of exactly AP or lateral, and the misalignment may be either axial or oblique. The pose of the C-arm (110) and the pose of the tracking device (129) and its related coordinate frame A are calculated by the localizing device (120) when the image is acquired. If the x-axis (134) or y-axis (135) of coordinate frame A is within, preferably, 30 degrees of the source-receiver axis of the C-arm (110), then the image is considered lateral or anteroposterior (AP) respectively.

If the acquired image is determined to be an AP view then, as shown in FIG. 3, the software will generate an AP version of the graphic representation (145) of the IM rod which is intended to highlight the transverse holes (131). This graphic representation (145) is defined relative to coordinate frame A, and is overlaid onto the AP image (126) of the IM rod (130). This AP version of the IM rod representation (145) comprises lines along the sides of the transverse holes' image (141), with dashed virtual lines extending from either side to emphasize the orientation of the holes (141). The drill guide representation (123) is displayed relative to the IM rod representation (145) as both are overlaid on the AP image (126) and improves the surgeon's ability to accurately align the drill guide (128) with the IM rod transverse holes (131) in the coronal plane.

If the acquired image is determined to be a lateral view then the software will optionally generate a lateral version of the graphic representation (144) of the transverse holes (131). This graphic representation (144) comprises two circles representing the openings of the two holes. It is overlaid on the transverse holes (141) seen in the lateral image (125) to improve the surgeons ability to identify the starting point for the drill. However, this is of less importance when compared to the utility of the cross-sectional graphic (127).

Alternatively, the graphic representation (124, 144 and 145) of the IM rod (131) may take other forms including 3-D surface models, bitmaps, or other wireframe models. Any version of the graphic representations (124, 144 and 145), regardless of view orientation, that provides the surgeon with sufficient information to orient the drill guide (128) relative to the IM rod (130) in a given plane may be used without departing from the instant invention.

Figure 4:
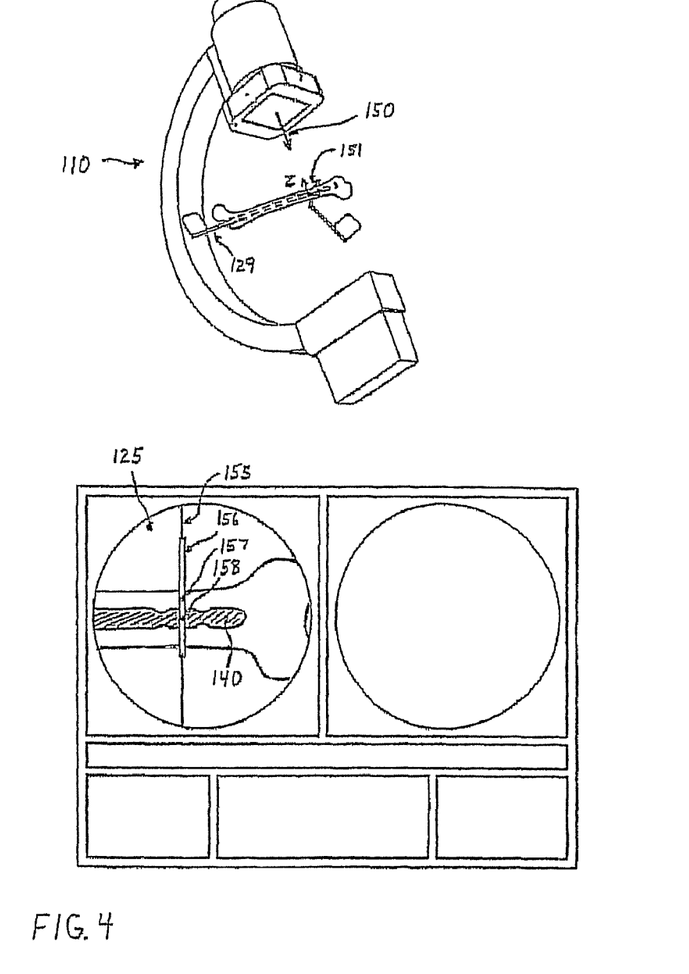
FIG. 4 is a perspective view of an intramedullary rod inserted into a femur, a tracked adapter attached to the intramedullary rod, a drill guide, a partial C-arm, and a example of a screen display of an image with superimposed graphics.

Additionally, as each image is acquired, adjustment of the position of the graphic representation (124, 144, and 145) of the IM rod (130) is performed to correct for any deviation due to flexure of the IM rod (131) or inaccuracies in attachment of the tracking device (129) or other conditions leading to inaccuracies in localizing the IM rod (130). Turning to FIG. 4, the poses of the IM rod tracking device (129) and the C-arm (110) are recorded at the time of image acquisition. If the C-arm source-receiver axis (150) is within, preferably, 30 degrees of the x-axis or y-axis of coordinate frame Z then adjustment is to be performed along the y-axis or x-axis, respectively. While the following adjustment steps are illustrated in FIG. 4, they are preferably performed without being displayed to the user. The adjustment is accomplished by projecting this adjustment axis (151) of the Z coordinate frame, onto the acquired image (125) using the conic projection model, and then analyzing the image data along a specific segment (156) of this projected line (155). Image processing techniques known to those skilled in the art threshold the image data within the image data segment (156) and find the center (158) of the radio-opaque IM rod image (140). The difference between this image location (158) and the projected origin (157) of coordinate frame Z is calculated and the difference value stored. Alternatively, any image processing techniques, or other means for directly measuring the positional error of the IM rod (130) at or near the transverse holes (131) may be used without departing from the instant invention.

When the difference value for AP, lateral, or both images have been processed, the corresponding Z frame x-axis and y-axis components are calculated by techniques known in the art. These difference components are then used to develop an adjustment transformation. Returning to FIG. 3, this adjustment transformation is applied to coordinate frame A, causing it to rotate such that the IM rod's AP and lateral graphic representations (144 and 145) defined relative to A, will align with the IM rod's x-ray images (140). After the adjustment rotations, the positions of the cross sectional representation (124), the AP representation (145), and the optional lateral representation (144), which are displayed to the user, more accurately represent the actual position of the IM rod (130).

Alternately, the overlay of the graphic representations (124, 144 and 145) may be corrected by the translation of coordinate frame A instead of by rotation. Or, instead, the graphic representations (124, 144 and 145) could be altered to effect the correction. For example, if the total difference is attributed to bending of the rod, the coordinate frame A could be left unchanged and the graphic representations (123, 144 and 145) could be altered to simulate the flexure of the IM rod (130). Any correction means that uses the difference between the expected and actual positions of the IM rod (130) to modify its graphic representation in such a way to make it more accurate may be used without departing from the instant invention.

Figure 5:
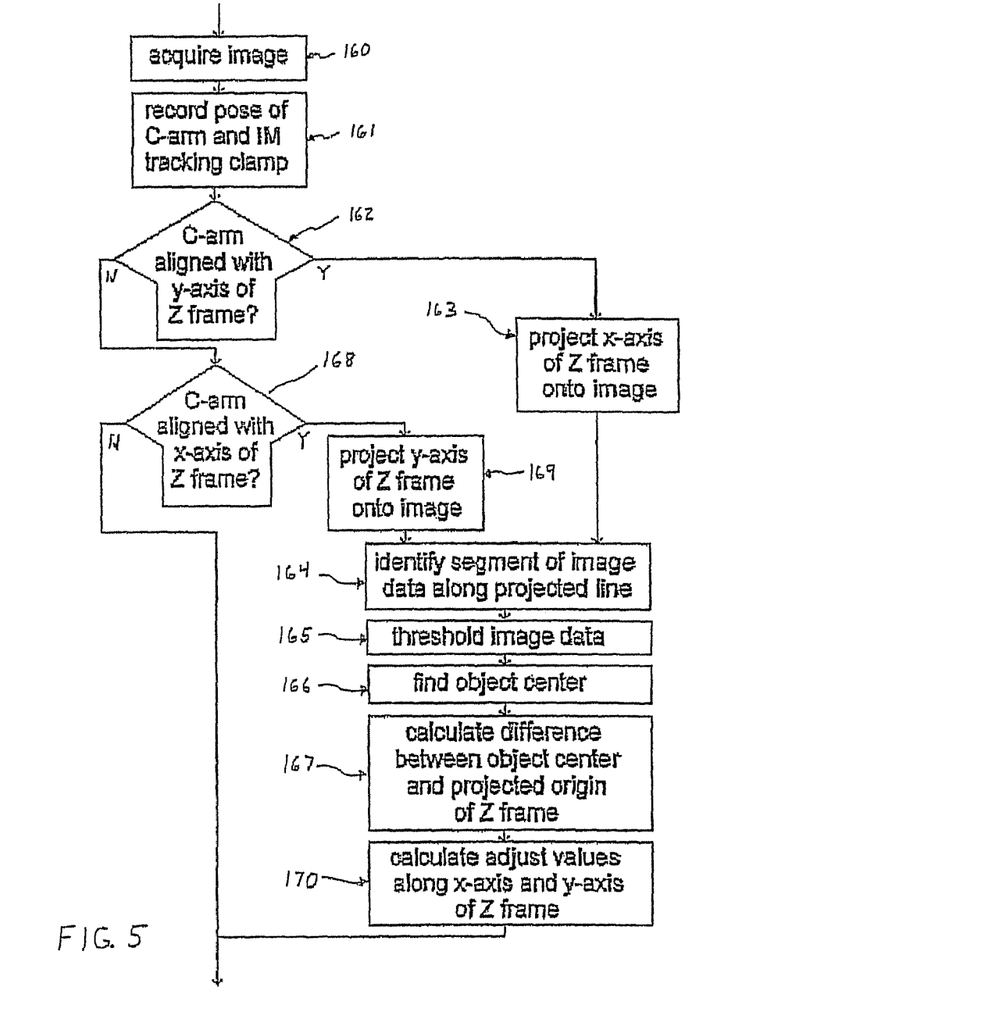
FIG. 5 is a diagrammatic illustration of the software operation during pose adjustment.

In summary, the software steps required are shown in FIG. 5. The image is acquired (160) and the poses of the C-arm and tracking clamp determined (161). If the y-axis of the Z coordinate frame is near-aligned with the C-arm (162) then project the Z frame x-axis onto the image (163), isolate an appropriate segment of image data along the projected line (164), apply a thresholding algorithm to emphasize the IM rod (165), find the center of the IM rod in the image data (166), and calculate the difference between the center of the IM rod's image and the projected Z-frame's origin as modeled (167). If the x-axis of the Z frame is near aligned with the C-arm (168) then project the y-axis onto the image (169) and perform the image processing steps above (164-167). Calculate an adjustment transformation based on available x-axis and y-axis difference values (170).

Returning to FIG. 1, once the corrected IM rod representations (124 and 144 and 145 seen best in FIG. 3) are being displayed, the surgeon prepares to drill the holes in the bone (131). The drill guide (128) generates a trajectory (123) that overlays both image fields (125 and 126) and projects onto the graphics field (127) as well. As shown in FIG. 3, the surgeon aligns the drill trajectory (123) to pass through the hole markers of the AP IM rod representation (145) and through the hole path on the cross sectional IM rod representation (124) in the graphics field (127). Once the proper alignment is achieved, the drill is advanced in the drill guide (128). The second hole is prepared in a similar fashion and confirmatory x-rays are obtained prior to inserting appropriately sized screws. Alternately, self-tapping screws may be directly inserted with a suitable instrument.

While the above description relates to the placement of interlocking screws in intramedullary rods placed in long bones, persons skilled in the art will recognize the applicability of this invention to other devices in other locations of the body such as the insertion of screws into other implantable devices. Any procedure wherein a first device is positioned relative to a second device at a position that is not known with sufficient accuracy by use of a localizing device can be performed in a more accurate manner with this invention.

The invention claimed is:

1. A computer assisted surgery system for accurately positioning device in a body, said system including:
    a localizing device configured to measure a pose of an implanted surgical device;
    an imaging device configured to acquire an image of said implanted surgical device;
    a computer configured to adjusted said pose for said implanted surgical device, said adjusted pose based on information developed from said image of said implanted surgical device,
    wherein said adjusted pose provides a compensation for an improperly positioned representation of said implanted surgical device over said acquired image.

2. The system of claim 1, wherein said implanted surgical device includes at least one of a surgical implant and a surgical instrument.

3. The system of claim 1, wherein said computer is configured to calculate a 3-D adjustment for said implanted surgical device, said 3-D adjustment calculated from a plurality of adjusted poses for said implanted surgical device, said plurality of adjusted poses each based on information developed from one of a plurality of images obtained from different viewpoints.

4. The system of claim 1, further including at least one of a drill guide, a drill guide pin, and a screw aligned with said implanted surgical device.

5. The system of claim 4, wherein said computer is configured to calculate a pose of at least one of said drill guide, said drill guide pin, and said screw relative to said implanted surgical device, said pose adjusted based on said adjusted pose of said said implanted surgical device.

6. The system of claim 5, wherein said computer is configured to calculate a 3-D adjustment of said pose, said 3-D adjustment calculated from plurality of adjusted poses of said drill guide, said drill guide pin, and/or said screw, said plurality of adjusted poses each based on information developed from one of a plurality of images obtained from different viewpoints.

7. The system of claim 1, wherein said compensation provides an accurate position of said implanted surgical device in said body.

8. The system of claim 1, further including a display configured to display an accurate representation of said implanted surgical device over said image, said representation based on at least said adjusted pose.

9. The system of claim 8, wherein said display includes an accurate representation of said surgical device relative to at least one representation of at least one other surgical device.

10. The system of claim 8, wherein said display is configured to display said representation in real time.

11. The system of claim 8, wherein said representation includes a line representative of a trajectory of said implanted surgical device.

12. The system of claim 8, wherein said representation includes at least one of a surface model, a solid model, a bitmap, and a wireframe model of said surgical device.

13. A method for accurately positioning a surgical device in a body, said method including:
    generating a computer model of said surgical device, said model including a reference point;
    measuring a pose of said surgical device with a localizing device;
    acquiring at least one image of said surgical device with an imaging device;
    using a computer to calculate a first position of said reference point based on at least said computer model and said pose of said surgical device;
    using the computer calculate a second position of said reference point based on at least said at least one image; and
    using the computer calculate an adjusted pose of said surgical device based on at least a difference between said first and second positions, wherein said adjusted pose includes a compensation for an improperly positioned representation of said surgical device in a graphical display of said surgical device.

14. The method of claim 13, wherein said surgical device includes at least one of a surgical implant and a surgical instrument.

15. The method of claim 13, wherein said step of using the computer to calculate said adjusted pose includes using the computer to calculate a 3-D adjustment of said surgical device, said 3-D adjustment calculated from a plurality of adjusted poses for said surgical device, said plurality of adjusted poses each based on information developed from one of a plurality of images obtained from different viewpoints.

16. The method of claim 13, further including aligning at least one of a drill guide, a drill guide pin, and a screw with said surgical device.

17. The method of claim 16, further including determining a pose of at least one of said drill guide, said drill guide pin, and said screw relative to said surgical device.

18. The method of claim 13, further including displaying an accurate representation of said surgical device over said image, said representation based on at least said adjusted pose.

19. The method of claim 18, wherein said displaying step includes displaying said accurate representation of said surgical device relative to at least one representation of at least one other surgical device.

20. The method of claim 18, wherein said displaying step occurs in real time.

21. The method of claim 18, wherein said representation includes a line representative of a trajectory of said surgical device.

22. The method of claim 18, wherein said representation includes at least one of a surface model, a solid model, a bitmap, and a wireframe model of said surgical device.

23. A method for improving the accuracy of a navigated surgical instrument, said method including:
    measuring a pose of an instrument and imaging device using a localizing device;
    acquiring at least one image of a patient anatomy and said instrument using said imaging device;
    using a computer to adjust said pose of said instrument using an adjustment transformation; and
    generating a graphic representation of said instrument based on said adjusted pose; wherein said adjustment transformation is based on positional errors at or near at least one end of the instrument determined from said at least one image of the patient anatomy and instrument.

24. The method of claim 23, wherein said representation of said instrument includes at least one of a surface model, a solid model, a bitmap, and a wireframe model.

25. The method of claim 23, wherein said adjustment transformation is determined by the following steps:
   projecting an adjustment axis onto said image;
   analyzing image data associated with said image along a segment of said adjustment axis in order to determine a projected center line of said instrument; and
   calculating a difference between said projected center line of said instrument and a measured center line of said instrument.

26. The method of claim 25, further including measuring said measured center line using the device.

27. The method of claim 25, wherein said projected center line corresponds to an origin of a coordinate frame defined relative to an exposed end of said instrument and located on said instrument at or near an end of said instrument inserted into a patient anatomy.

28. The method of claim 23, further including acquiring a plurality of images from different viewpoints,
   wherein said adjustment transformation includes a 3-D adjustment for said instrument, said 3-D adjustment calculated from a plurality of adjusted poses for said instrument, said plurality of adjusted poses each based on information developed from one of said plurality of images from different viewpoints.

29. The method of claim 23, wherein said using said computer to adjust step includes applying said adjustment transformation to a coordinate frame defined at an interface between said instrument and a tracking device attached to said instrument.

* * * * *